(12) United States Patent
Shell et al.

(10) Patent No.: US 10,933,153 B2
(45) Date of Patent: *Mar. 2, 2021

(54) SYSTEMS AND METHODS FOR SECURE DELIVERY, TRANSFER, STORAGE, AND RETRIEVAL OF ITEMS

(71) Applicant: DLVR, LLC, Boulder, CO (US)

(72) Inventors: Michael Ross Shell, Niwot, CO (US); Sameer Goswami, Millburn, NJ (US)

(73) Assignee: DLVR, LLC, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/840,335

(22) Filed: Apr. 4, 2020

(65) Prior Publication Data
US 2020/0237946 A1    Jul. 30, 2020

Related U.S. Application Data

(63) Continuation-in-part of application No. 16/678,891, filed on Nov. 8, 2019.

(60) Provisional application No. 62/758,101, filed on Nov. 9, 2018, provisional application No. 62/883,996, filed on Aug. 7, 2019.

(51) Int. Cl.
*A61L 2/28* (2006.01)
*A61L 2/22* (2006.01)
(Continued)

(52) U.S. Cl.
CPC .............. *A61L 2/28* (2013.01); *A47G 29/141* (2013.01); *A61L 2/04* (2013.01); *A61L 2/10* (2013.01); *A61L 2/20* (2013.01); *A61L 2/22* (2013.01); *G07C 9/00896* (2013.01); *A47G 2029/145* (2013.01); *A47G 2029/147* (2013.01); *A47G 2029/149* (2013.01); *A61L 2202/11* (2013.01); *A61L 2202/14* (2013.01); *A61L 2202/15* (2013.01); *A61L 2202/23* (2013.01); *G07C 2009/0092* (2013.01)

(58) Field of Classification Search
None
See application file for complete search history.

(56) References Cited

U.S. PATENT DOCUMENTS 9,861,221 B2    1/2018    Jiang
10,039,401 B1   8/2018    Romanucci
(Continued)

OTHER PUBLICATIONS

The Porch Pod. https://www.theporchpod.com/. Believed to have been sold as early as Jul. 31, 2019. 10 pages.
(Continued)

*Primary Examiner* — Adolf Dsouza
(74) *Attorney, Agent, or Firm* — FisherBroyles, LLP; Ian R. Walsworth; Craig W. Mueller

(57) ABSTRACT

Systems and methods for securely delivering, transferring ownership, storing, accessing and receiving or returning an item from another are disclosed herein. In one embodiment, a system and method are provided to securely receive a variety of different sizes and types of packages at one or more locations, including but not limited to on or adjacent a recipient's property. In another embodiment, the system and method allow a user to receive, store and/or return an item without exposing the item to loss, damage, spoilage or other events that would impair the value of the items. Methods of utilizing the systems described herein are also disclosed.

24 Claims, 12 Drawing Sheets

(51) Int. Cl.
*A61L 2/20* (2006.01)
*A61L 2/10* (2006.01)
*A61L 2/04* (2006.01)
*A47G 29/14* (2006.01)
*G07C 9/00* (2020.01)

(56) References Cited

U.S. PATENT DOCUMENTS

| | | | |
|---|---|---|---|
| 10,743,694 | B2 | 8/2020 | Raphael et al. |
| D897,625 | S | 9/2020 | Hall et al. |
| 2006/0008400 | A1* | 1/2006 | Gutman .............. A61F 13/00 422/292 |
| 2016/0068277 | A1 | 3/2016 | Manitta |
| 2016/0101874 | A1 | 4/2016 | McKinnon |
| 2017/0116568 | A1 | 4/2017 | Pleis |
| 2017/0147975 | A1 | 5/2017 | Natarajan et al. |
| 2018/0130017 | A1 | 5/2018 | Gupta |
| 2018/0133583 | A1* | 5/2018 | Tran .................. H04W 84/18 |
| 2019/0277552 | A1* | 9/2019 | Vu .................... F25D 23/025 |
| 2019/0297045 | A1* | 9/2019 | Orsini ................ H04W 4/024 |

OTHER PUBLICATIONS

Door Box. https://www.doorbox.co/?gclid=Cj0KCQiAk53-BRD0ARIsAJuNhpulnD8O-SahYXGpI6J-5RVEcCcOrN-A05q2idy7wMzMeYFwTRijy1VkaAryXEALw_wcB. Believed to have been sold as early as Jan. 2017. 19 pages.

Landport. https://www.thelandport.com/. Believed to have been sold as early as May 29, 2014. 9 pages.

Bench Sentry. https://benchsentry.com/. Believed to have been sold as early as Aug. 1, 2016. 13 pages.

Dynosafe. http://www.dynosafe.com/. Believed to have been sold as early as 2018. 10 pages.

BoxLock. https://www.getboxlock.com/. 6 pages.

ParcelGuard. https://www.danbyparcelguard.com/en-us/. Believed to have been sold as early as Jan. 8, 2019. 11 pages.

Elephantrunk II. https://www.architecturalmailboxes.com/product/the-elephantrunk-ii/. Believed to have been sold as early as 2012. 6 pages.

Fred—Drone Delivery Made Simple. https://www.freddeliverybox.com/. Believed to have been sold as early as Sep. 17, 2019. 23 pages.

Porch Box. https://www.porch-box.com/how-it-works. 21 pages.

Eufy Security. https://www.kickstarter.com/projects/smart-drop/take-control-over-your-deliveries-with-eufy-smart-drop?utm_source=kickbooster-direct&utm_medium=kickbooster&utm_content=link&utm_campaign=1d077b39. Product believed to be launched Aug. 25, 2020. 48 pages.

Andrew Silver. "RFID + Camera + Lock = Smart Mailbox." https://spectrum.ieee.org/tech-talk/consumer-electronics/gadgets/rfid-camera-lock-smart-mailbox. Nov. 1, 2016. 5 pages.

Parcel Home. https://www.parcelhome.com/. Believed to be on sale since 2014. 13 pages.

* cited by examiner

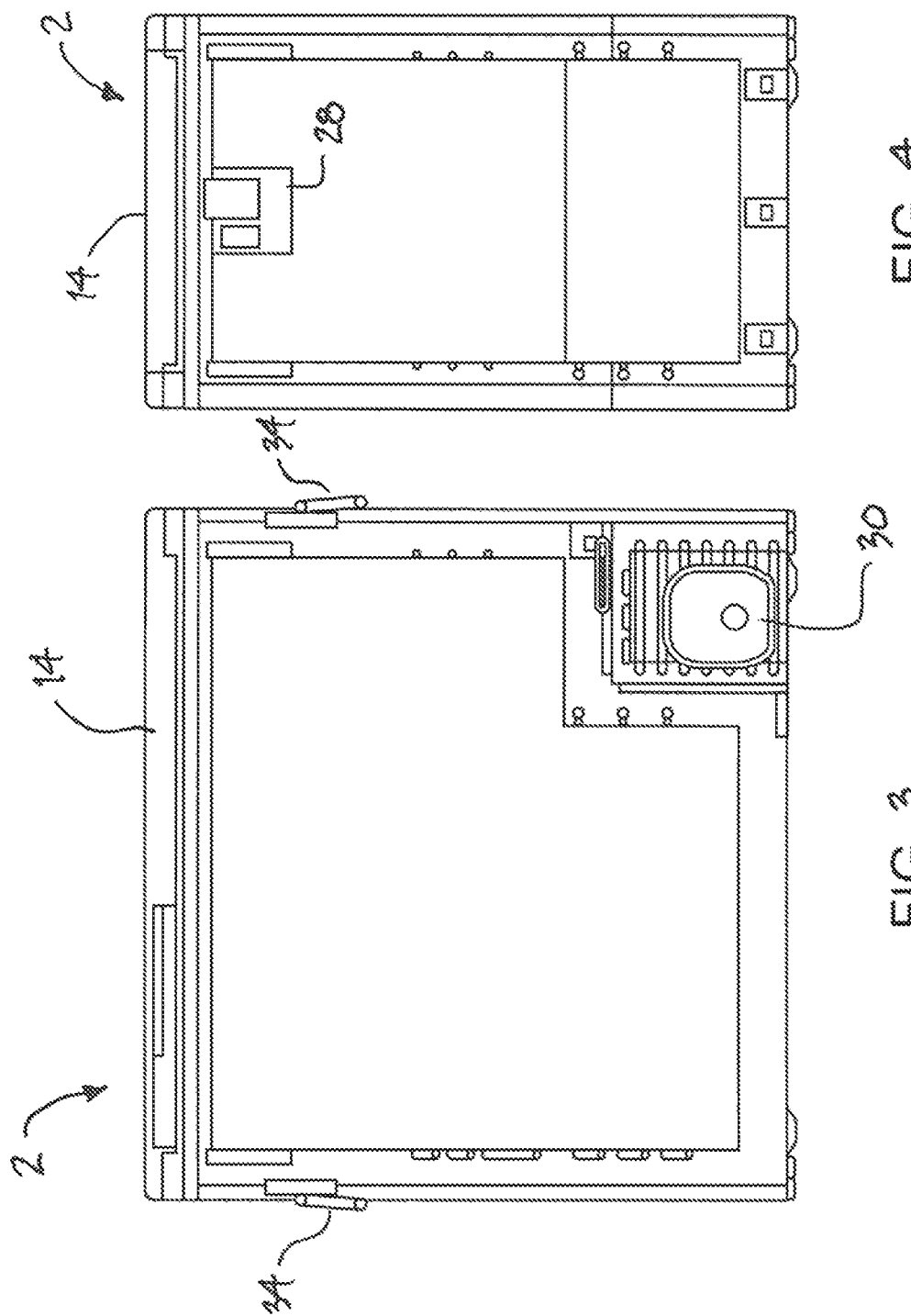

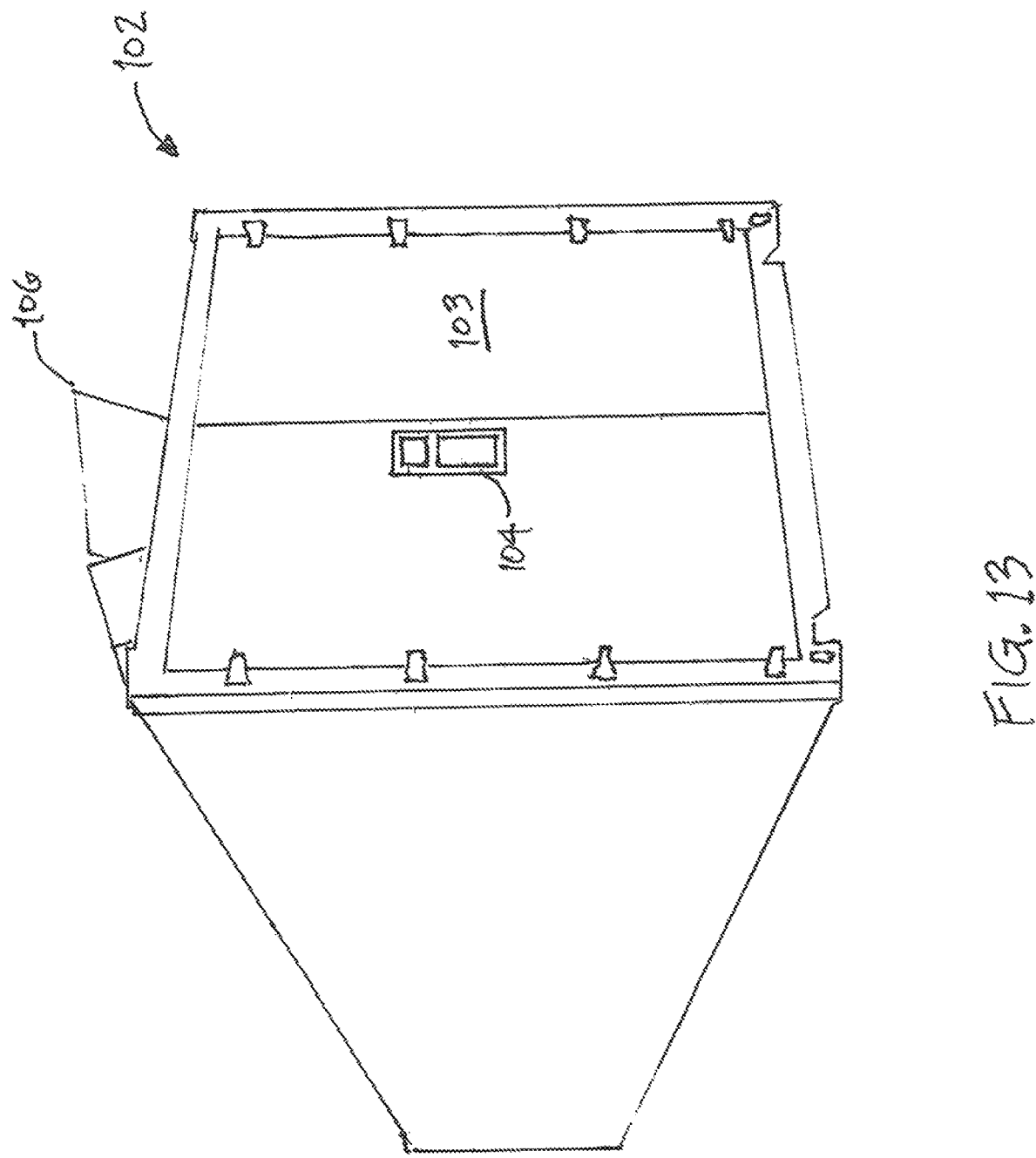

SYSTEMS AND METHODS FOR SECURE DELIVERY, TRANSFER, STORAGE, AND RETRIEVAL OF ITEMS

This application is a continuation-in-part of U.S. patent application Ser. No. 16/678,891, filed Nov. 8, 2019, which claims the benefit of U.S. Provisional Patent Application Ser. No. 62/758,101, filed Nov. 9, 2018, and U.S. Provisional Patent Application Ser. No. 62/883,996, filed Aug. 7, 2019, the entireties of which are incorporated by reference herein.

FIELD OF THE INVENTION

Embodiments of the present invention are generally concerned with software and hardware systems and methods for delivery of items, such as household or commercial goods and other e-commerce items.

BACKGROUND

Package volume has grown from 44-billion parcels in 2014 to 65 billion in 2016, according to a Pitney Bowes index that measures volume and spending on shipments in 13 major markets including the United States. The index estimates package shipping will continue to rise between 17% and 28% each year between 2017 and 2021. It follows that package theft has become an epidemic. More specifically, over 11-million packages are stolen from doorsteps in the United States each year. In addition, over 1-billion packages are not successfully delivered on the first attempt. These two issues result in over $17-billion in losses per year. The predominant challenge currently faced is associated with scheduling and executing a secure handoff between a carrier and recipient that meets the recipient's needs while aligning with evolving delivery methods and processes.

While certain systems and methods have attempted to resolve these issues, the primary challenges associated with scheduling and executing a secure handoff between a carrier and recipient remain. For example, U.S. Patent Application Publication Nos. 2016/0068277 and 2016/0101874 describe a platform or tray that may support a package, a drone, or a combination of the two. While these publications address concerns relating to access and security, they do not address loss or spoilage and still leave the package and/or drone exposed and, thus, subject to theft. U.S. Patent Application Publication No. 2017/0116568 describes a container with moveable gates for securing a package but fails to ensure the package is not damaged or spoiled while in the container.

In addition, the Internet of Things ("IoT") and Blockchain technology has enhanced the way in which users access data associated with remote devices and, in certain instances, remotely control such devices. While numerous solutions have attempted to improve upon IoT network communications, device, and data security, particularly with respect to package delivery, receipt, and item storage, deficiencies still persist. These prior solutions generally fail to provide a way for sharing access via Blockchain and/or control of an IoT capable device over a closed network.

Further, the current e-commerce ecosystem does not capture the complete information of a household or commercial establishment's purchasing behavior, and the limited information is distributed amongst various e-commerce players in a piecemeal fashion. The present invention comprises an ecosystem that captures the complete information of household or commercial buyer behavior, agnostic of the e-commerce website from which the product is ordered or returned to. The ecosystem of the present disclosure also aims to share information to and from the delivery companies, thus completing the exchange and closing the loop on eCommerce transactions. The data captured during this process permits a user of the system to obtain a complete profile of household or commercial establishment's purchasing patterns, and in turn, drive efficiencies in targeted marketing communication to end-users. From this data, algorithms, analysis, optimization, cost-savings, incentives, and many other value-adds can be realized and/or offered back to delivery companies and the end-users.

Given these and other shortcomings of the prior art, there is a long-felt but unresolved need for systems and methods that meet varying customer's needs and that integrates with the current and planned delivery and collection modalities while aligning with existing carrier processes. It is also desirable to provide systems and methods that avoid loss not only attributable to theft, including but not limited to, spoilage or damage from the elements.

SUMMARY

It is one aspect of some embodiments of the present invention to provide a secure and transparent product shipping system. The system accommodates receiving customer delivery time preference, address, delivery means, package size, and required temperature conditions, while fully empowering the customer to control physical and temporal access to the delivery area.

It is, therefore, one aspect of embodiments of the present invention to provide a recipient and carrier with a centralized hardware and software system that allows management of the delivery and collection process. One embodiment of the present invention provide at least one of a means for 1) securely ordering goods, which includes automated input of shipping and delivery instructions; 2) securely receiving a variety of different package sizes and types at one or more locations, including, but not limited to, on or adjacent to a recipient's property; 3) tracking package shipment and delivery and receipt confirmation or notice of non-receipt of the same; 4) providing a carrier an interactive modality for receiving and granting access to a container or like vessel; 5) ensuring items within a package are safe from loss, damage, spoilage, and other conditions or events that cause to adversely affect the value of the items; 6) interacting with carriers, to manage the delivery process, to change delivery instructions while in transit, if necessary, to receive the delivery as desired; 7) interacting with carriers, to manage the returns process, to change return instructions while in transit, if necessary; and 8) offering carriers a secure interactive platform to share information. The use of "package" herein is not limiting and one of ordinary skill in the art will appreciate that the devices, methods, and systems described herein contemplate use with envelopes and parcels regardless of size, weight, or shape.

One embodiment of the present invention is a centralized system comprised of system software integrated with a storage container. In some embodiments, at least one container or like vessel is positioned on or adjacent to a recipient's property, such as a home, a porch, a backyard, an office, a rental property, a common area, curb, sidewalk, catwalk, factory or warehouse, etc. The container may be owned and/or dedicated to a single user, business, or household. In other embodiments, the container or vessel is located at a convenient public or semi-public location, such as a post office, a local supermarket, a library, a local recreational or community center, a church, a residential mailbox station, a curbside, a designated area of a parking lot, a school, a playground, or other semi-public or public location, wherein the container may be temporarily used by the intended recipient and accessible to other users as well. The third-party owners of these locations could charge a small fee to provide this contemplated pickup service. The container may be fixed or transportable from a first location to a second location.

The packages to be received and stored in the container may encompass a variety of consumer goods, including apparel, electronics, books/magazines, gift items, personal items, mail, groceries, alcohol, pharmaceuticals and other legal recreational drugs, hazardous materials, foodstuffs, etc. In some embodiments, the container may be large enough to store furniture, home décor items, exercise equipment, and other larger goods. In other embodiments, the container may be of very significant size, or akin to a storage unit for receiving and storing any variety of business goods for commercial use. The system of one embodiment assesses the size and shape of the package, either from indicia found on the package or sensed, and provides access to an appropriately sized container. Some embodiments of the present invention contemplate autonomous or semi-autonomous rerouting of packages under certain circumstances. For example, if the recipient's container cannot accommodate the size or character of the package, the carrier—human or autonomous—will be directed to a suitable nearby container or secure location, such as a neighbor's container that has been preauthorized for such deliveries (or a garage or other suitable space).

If no suitable delivery locations are identified within a predetermined radius of the resident's primary delivery location, the carrier will be directed to deliver the package to a public or semi-public delivery location as described above. Again, the alternate delivery decisions can be autonomous, preselected by the recipient, or made real-time by the recipient on their mobile device, for example. In still other embodiments, the system will similarly obtain information regarding temperature requirements and open the appropriate container and initiate a temperature increase or decrease. The power for this functionality can be provided by an external power source or integrated solar panels.

The container may comprise a first access portal for receiving one class of consumer or business items, such as a package, and a second access portal for receiving smaller items, such as mail. Further, perishable items may be stored in a first container or container partition, while non-perishable items may be stored in a second container or container partition.

The container may comprise an interactive keypad, or other physical, in-direct, remote, or virtual data input device or method, associated with a structure's main door, a garage, an entry gate, a vehicle, or a designated office/commercial storage area. Entering a code, for example, into the data input device will allow access to the storage container. Alternatively, the package may include indicia, a transmitter, or related device that is assessed by the container, or which communicates with the container, to provide permission-based access to the container's door, the garage, the entry gate, the vehicle, the designated office/commercial storage area, etc. to allow for package delivery.

The packages may have a unique code, circuit, RFID transmitter, coil, microchip, or display a UPC code, a QR code, or similar indicia that is confirmed before the container permits access thereto. The confirmation may occur autonomously by scanning or reading a unique code on the package, while in other embodiments, the confirmation may occur through a user-selected confirmation sequence. In some embodiments, facial recognition is used to allow delivery personnel or preselected third parties to access the container.

The container is accessed by human carriers or autonomous delivery devices, including drones, driverless vehicles, robots, etc. In other embodiments, the one or more containers or like vessels may be accessed by a person with appropriate credentials to access and deposit items within the same. As mentioned above, the container may comprise a keypad, an RFID reader/scanner, a chip reader, an infrared scanner, a proximity scanner, a biometric scanner, or other security systems known to those of ordinary skill in the art. The containers and systems described herein may also employ Near-Field Communication (NFC) technology. The container may have the ability to grant permission-based access to a garage door, home door, automobiles, designated office areas, warehouse or other permanently or temporarily secure areas.

In other embodiments, the container employs one or more cameras, a GPS locator device, a motion detector, and/or a charging dock for drones and delivery robots. A version may have the ability to accept deliveries from drones, voorloopers (such as in the case of delivery to a high-rise apartment building), or via a window-based receptacle, which may be translucent. In some embodiments, the container includes audio output devices that provide prerecorded or real-time instructions to the carrier—"please place package A in compartment A, please place package B in refrigerated compartment B" or equivalent instructions. In other embodiments, the parcels within the container are coded (using RFID-coded labels, for example) for extraction and placement in a particular location within the secure area. In this manner, an autonomous delivery device (i.e., drone) may deliver different types of items and securely store those items in the appropriate areas or zones within a receptacle, such as a secure container described in greater detail herein. This functionality is particularly well-suited for grocery or pharmaceutical delivery services, wherein some items are to be stored at different temperatures. Real-time audio may be generated via the recipient's mobile device or remote computer.

It is another aspect of some embodiments of the present disclosure to provide software provided with a computer-readable storage medium (preferably non-transitory) comprising processor-executable instructions operable to utilize the systems or perform the methods as described herein. The software may be installed on a mobile application that allows users to monitor and/or control container access. In some embodiments, a carrier may have certain use rights granted by the user and managed through the mobile application or a similar application.

In some embodiments, the software solution includes, but is not restricted to, a mobile application, wherein a browser-based application that connects all the components of the complete product delivery value chain. The system may comprise an e-commerce website, the corresponding delivery service for the ordered product, and the relevant container or receptacle that accepts the delivery. All the components will preferably be connected via a cloud computing platform via Blockchain, IoT, or software as described herein. In other embodiments, the software solution will offer a one-click solution for providing the relevant delivery information and will generate an order confirmation, tracking details, and communicate container access authorization information, and successful receipt or pickup. In some embodiments, the relevant delivery tracking information can be accessed via a voice-controlled device like Alexa or Siri.

In some embodiments, the foregoing may be used to transfer ownership of items between two private parties at a secure location or facilitate charitable donations.

Currently, a shipping and tracking code is generated after an order is placed via a website, for example. Some web-based marketplaces require package carriers to notify recipients within a predefined window of delivery time. The carrier is often also asked to scan the package or otherwise notify the shipper the package has been delivered, so the marketplace can notify the recipient. Embodiments of the present invention improve on this method by also including an indication of the container's location. When the human or automated carrier scans the package and forwards that information to the container, or when the container scans or otherwise recognizes the package, the container unlocks and/or opens to receive the package. Thereafter, the system notifies the recipient that the package has been delivered and secures the container. Accordingly, continuous and secure package delivery is possible.

It is one aspect of some embodiments of the present invention to provide a secure package receipt system that is stored on a domicile porch or any similar building entrance location. As in the other embodiments described herein, the contemplated system protects packages from the elements, allows for secure handoff/notification, secure storage, and, in some embodiments, climate control to keep refrigerated or frozen items cold and fresh. The climate-controlled storage compartment employed by some embodiments receives power via a direct connection to the dwelling or building's power or a battery. In other embodiments, dedicated solar panels are provided. In some embodiments, the system will employee scales, cameras, or other sensors to recognize weight, volume, and temperature of the contents inside to trigger a refrigeration or freezer element if needed. As eluded to above, alternative delivery methods are also contemplated that enable seamless driverless vehicle, robot, and/or drone delivery. Additionally, standard mail can be delivered in a dedicated slot.

With respect to security, the system may be anchored to the porch or structure and may include a backup battery that initiates an alarm or sends a notification when the container is unplugged to hinder theft or notify the user that power has been lost. If the user is moving the box intentionally, the alarm can be disabled wirelessly at any time through a web application, or by entering a code. Additionally, GPS may be integrated to pinpoint the location of the container.

The container can be insulated and weatherproof. In addition, wired or wireless means for communicating with the dwelling or building's internet network or a mobile chip, for example, may be provided. The container of some embodiments allows remote opening with a garage door opener, a smartwatch, a mobile application, etc. Child safety measures, such as motion detectors or voice-activated controls associated with the container are employed to prevent small children from being trapped. The container may also double as a bench and include charging docks for mobile devices or drones.

In one embodiment, the "container" is a garage that selectively opens when prompted by the carrier, e.g., upon entry of a code, facial recognition confirmation, etc., or autonomously when the package is scanned. Thereafter, the recipient is notified regarding entry into the garage and the package delivery. The system may initiate garage door closing after a predetermined time. Further, entry into the garage may initiate cameras that monitor the carrier's activities within the garage. This system may also include audio capabilities that allow the recipient to direct the human or automated carrier as to where to leave the package—on the floor, on a shelf, in a cabinet, in the refrigerator, etc. This information could be comprised of pre-recorded messages or real-time via the recipient's mobile device, for example.

In another embodiment, the container is a separate secure area, such as a shed, that receives and securely stores a package or parcel until the purchaser returns to retrieve the same. The package can be placed within the shed or deposited through a chute on the shed roof, for example. If the package is to be delivered through the shed's door, the aspects described above with respect to garage delivery can be employed. In some instances, the package is deposited in a separate container in the shed. The shed, or integrated container positioned therein, may be refrigerated. In the roof delivery option, which is primarily suited for drone delivery, the shed's roof may be completely or partially retractable.

In yet another embodiment, the container is similar to a curbside mailbox and allows human or drone package delivery. This iteration may have refrigeration capabilities and can be positioned above or below ground. The above-ground version can be attached to, or replace current single or multi-unit mailboxes. The below-ground version can be selectively deployable to an above-ground position of use, wherein the devices that allow selective access to the container may be additionally used to lift the container for convenient package delivery. One of ordinary skill in the art will appreciate that the methods that allow selective access to the container, container monitoring, delivery notification, and container environmental control described above can also be employed in this embodiment of the present invention.

In still yet another embodiment, the container comprises an extension of a dwelling or a business's entrance. Here, the extended entrance is similar to a mudroom configured to receive packages, similar to the embodiments described above.

A dwelling or business can also be modified to facilitate aerial drone package delivery. More specifically, a retractable roof door may be provided that selectively opens when a drone approaches or hovers over it. Thereafter, the drone lowers the package onto a stationary platform or lands on the platform for charging. After the package is delivered and the drone departs, the platform retracts, and the package is lowered into the dwelling. Packages could also be picked up from the same system.

A simplified version of the present invention is a stand-alone box that receives the package as contemplated herein. The box would be openable only by the human or robotic carrier and the recipient. Indeed, in some embodiments, the carrier delivers the box and included package to a predetermined secure location, wherein the box is retrieved at a later time. This embodiment could allow for various commercial, military and disaster relief use cases. In other versions, the box is selectively secured or tethered to a building, for example.

It is another aspect of many of the embodiments of the present invention discussed above to facilitate delivery of some types of packages. For example, some packages—wine, legal documents, expensive items—require a signature before the package will be released, which means the recipient must be present. Carriers will normally attempt to deliver such packages 2-3 times before the intended recipient must travel to a distribution center to obtain their package. Such packages can be delivered to the containers as described herein, thereby avoiding this very common inconvenience.

It is another aspect of some embodiments of the present invention to provide a container configured to disinfect or otherwise expose packages stored within to a disinfecting environment. For example, the container may include devices that selectively treat stored items with an aerosolized mist of disinfectant solution. The disinfectant solution may be stored within a bottle associated with the container that may be refillable. Alternatively, the user may also place a disinfecting device, such as a puck that releases disinfecting material for a predetermined amount of time; when heated with a heat source; when exposed to UV or microwave radiation; etc. A vent or venting system may be provided to facilitate removal of the disinfectant solution or material. The contemplated disinfecting mist may be provided by at least one sprayer or nozzle interconnected to at least one of the inner surfaces of the container walls, the container floor, and the inner surface of the lid or top. In one embodiment, the nozzles are interconnected to a reservoir of disinfecting material and the mist is selectively controlled by a control system configured to direct disinfecting material from the reservoir to the at least one nozzle by controlling a valve and/or atomizer, for example. One of skill in the art will appreciate that the container may be purged with inert gas or gas harmful to pathogens (carbon dioxide, for example) to create the disinfecting environment.

Other embodiments expose stored items to ultra-violet (UV) or microwave radiation for a predetermined amount of time. The UV radiation may be naturally occurring, wherein the container includes one or more translucent or mesh panels that allow sunlight to enter into the container. The contemplated UV-based system of one embodiment comprises at least on UV emitter interconnected to at least one of the inner surfaces of the container walls, the container floor, and the inner surface of the lid or top. A controller is provided that is configured to selectively power the at least one UV emitter.

Depending on the character of the package, the container may also employ heating or refrigeration capabilities that increase or reduce the temperature within the container to destroy pathogens. As one of skill in the art will appreciate, a control system described herein may also be employed to control container temperature. Further, the controllers of the systems described herein may function on a timer, be manually adjusted, or be adjusted with a device remote to the container. The container may also be configured to provide selective pressure variations to create and maintain a negative pressure or vacuum within the container. The disinfecting functionality employed by some embodiments of the present invention may be integrated into any of the container embodiments discussed herein.

In operation, the container is unlocked in the manner described herein before package receipt. The container may also be configured to automatically open and close so that the carrier or the end-user does not need to touch the container lid. After the package is placed within the container, it is closed, locked, and disinfecting of the stored items begins. One of ordinary skill in the art will appreciate that some embodiments, e.g., those with compartments that receive postage, may not require the open/closing and locking steps. Disinfecting of the stored package is done for a predetermined amount of time that is controlled remotely by the shipper, the end-user, or by a timer-based control system associated with the container that disinfects the container's storage area according to guidelines preset by the end-user, shipper, or a third party. In some embodiments, the door or doors of the container are locked during the disinfection process to prevent unintentional opening. The end-user is notified that their package is safe from pathogens after the disinfection process is complete. Some embodiments also include the functionality wherein the package is tested after disinfection to verify the package is free from pathogens or pathogens have been reduced below a recommended level. Further disinfection or a different disinfection method or protocol can be implemented if needed.

The Summary of the Invention is neither intended nor should it be construed as being representative of the full extent and scope of the present invention. That is, these and other aspects and advantages will be apparent from the disclosure of the invention(s) described herein. Further, the above-described embodiments, aspects, objectives, and configurations are neither complete nor exhaustive. As will be appreciated, other embodiments of the invention are possible using, alone or in combination, one or more of the features set forth above or described below. Moreover, references made herein to "the present invention" or aspects thereof should be understood to mean certain embodiments of the present invention and should not necessarily be construed as limiting all embodiments to a particular description. The present invention is set forth in various levels of detail in the Summary of the Invention as well as in the attached drawings and the Detailed Description and no limitation as to the scope of the present invention is intended by either the inclusion or non-inclusion of elements, components, etc. in this Summary of the Invention. Additional aspects of the present invention will become more readily apparent from the Detailed Description, particularly when taken together with the drawings. In many cases, the foregoing examples of containers for residential or home use may also apply to commercial, business, office, and other possible use cases. Additionally, the containers enable secure receipt of packages while enabling storage for secure pickup of packages by authorized human, drone, robot, etc.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatically" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "machine-readable media" as used herein refers to any tangible storage that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a flexible disk, hard disk, magnetic tape, or any other magnetic medium, magneto-optical medium, a CD-ROM, any other optical medium, a RAM, a PROM, an EPROM, a FLASH-EPROM, a solid-state medium like a memory card, any other memory chip or cartridge, or any other medium from which a computer or like machine can read.

When the computer-readable media is configured as a database, it is to be understood that the database may be any type of database, such as relational, hierarchical, object-oriented, and/or the like. Accordingly, the invention is considered to include a tangible storage medium and prior art-recognized equivalents and successor media, in which the software implementations of the present invention are stored.

The terms "determine", "calculate", and "compute," and variations thereof, as used herein, are used interchangeably and include any type of methodology, process, mathematical operation or technique.

The term "module" as used herein refers to any known or later developed hardware, software, firmware, machine engine, artificial intelligence, fuzzy logic, or combination of hardware and software that is capable of performing the functionality associated with that element. Also, while the invention is described in terms of exemplary embodiments, it should be appreciated that aspects of the invention may be separately claimed.

The term "Internet of Things" or "IoT" as used herein refers to a system of devices capable of communicating over a network, including the communications of data over the network. The devices can include everyday objects such as thermostat systems, door locks, doors, garage door openers, security devices, cameras, appliances, and other devices able to connect to a network.

BRIEF DESCRIPTION OF THE DRAWINGS

The accompanying drawings, which are incorporated in and constitute a part of the specification, illustrate embodiments of the invention and together with the general description of the invention given above and the detailed description of the drawings given below, serve to explain the principles of these inventions.

FIG. 3 is a front cross-section of one embodiment;

FIG. 4 is a side cross-section of the embodiment shown in FIG. 3;

FIG. 13 illustrates an embodiment of the present disclosure for transporting business or consumer items in a commercial container.

The accompanying drawings, which are incorporated in and constitute a part of the specification, illustrate embodiments of the invention and together with the general description of the invention given above and the detailed description of the drawings given below, serve to explain the principles of these inventions.

DETAILED DESCRIPTION

The present disclosure, in varying embodiments, relates to systems and methods for securely delivering, transferring ownership, storing, accessing, and receiving an item from another. In one embodiment, for example, a system and method are provided to securely receive a variety of different sizes and types of packages at one or more locations, including but not limited to on or adjacent a recipient's property or at a commercial or industrial location. In yet other embodiments, the system and method permits a user to track the shipment and delivery of a package and confirm receipt of the same from any location, thereby ensuring that the package has arrived at the correct location and is securely stored until the user returns to the delivery location to retrieve the item. In further embodiments, the system may comprise an interactive modality for receiving and granting access to a container that is owned or at least temporarily dedicated to a particular user. And in other embodiments, the system and method allow a user to receive or send and store an item without exposing the item to loss, damage, spoilage, or other events that would impair the value of the items. The same logic applies to protection of an item prior to it being picked up.

The ensuing description provides embodiments only and is not intended to limit the scope, applicability, or configuration of the claimed invention. Rather, the ensuing description will provide those skilled in the art with an enabling description for implementing the embodiments. It should be understood that various changes may be made in the function and arrangement of elements without departing from the spirit and scope of the appended claims.

Furthermore, while embodiments of the present disclosure will be described in connection with various examples or illustrations, it should be appreciated that embodiments of the present disclosure are not so limited. In particular, embodiments of the present disclosure may be applied to any location and any item, whether owned/purchased or not. For instance, while embodiments of the present invention may be described with respect to a single-family residence or commercial property, other applicability is contemplated. It should be understood that the embodiments described herein are for illustrative purposes and should not be construed as limiting the present disclosure.

Figure 1:
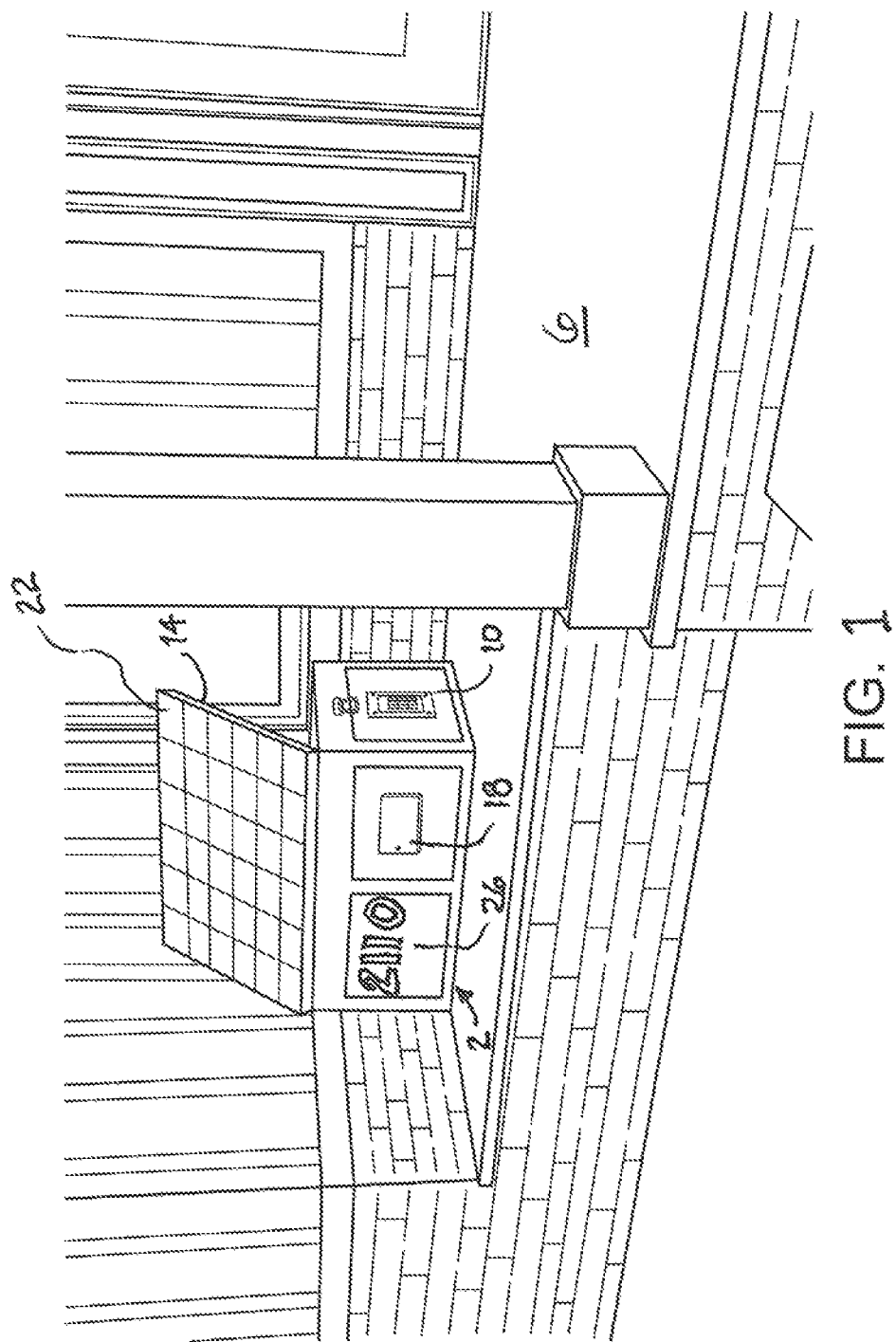
FIG. 1 illustrates one embodiment of the present invention positioned on a porch.
Figure 2:
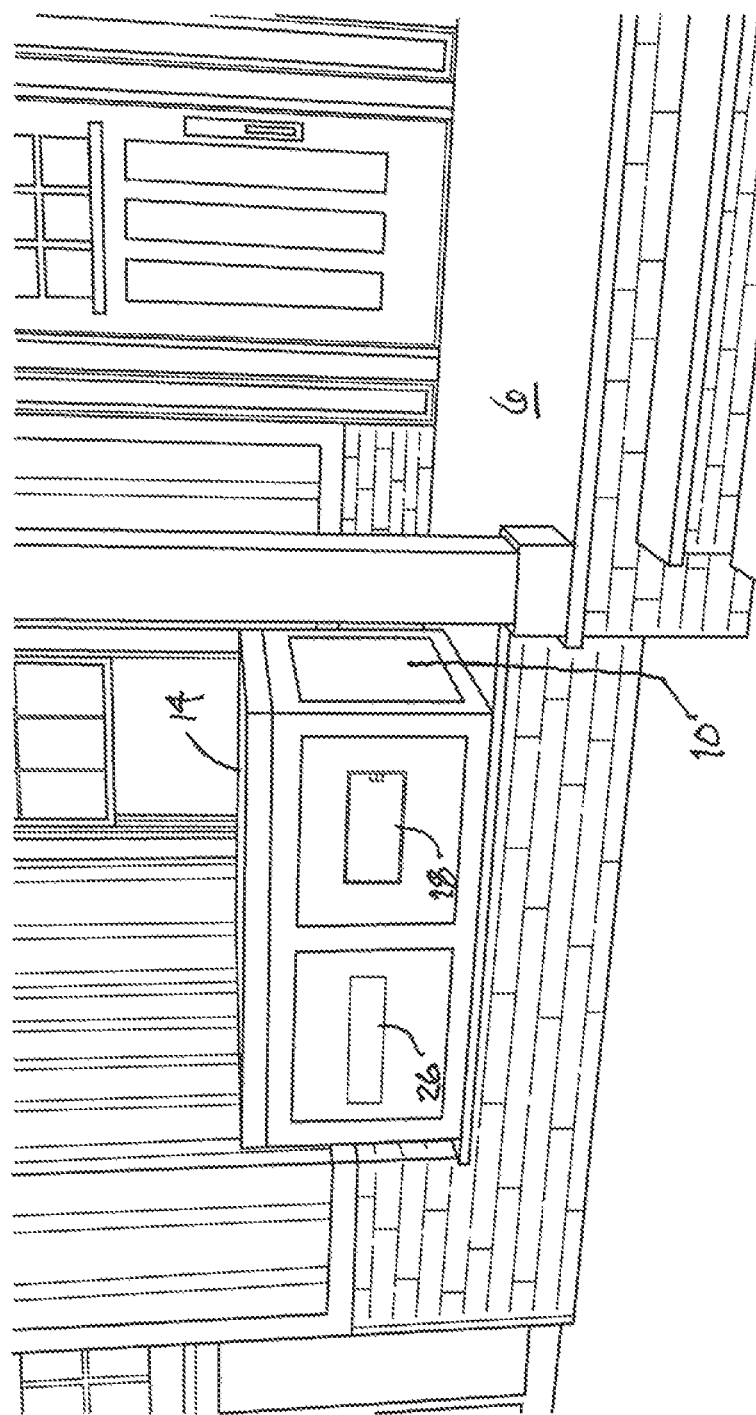
FIG. 2 is another illustration of the embodiment shown in FIG. 1.

FIGS. 1 and 2 show one embodiment of the present invention comprising a container 2 located on a porch 6, stoop or entryway of a residential property. The container 6 comprises a keypad 10 that permits a user to enter a code to open the access portal 14 of the container 2. Here, the access portal 14 is located on the top surface of the container 2 that is selectively accessed by pivoting the top cover of the container 2 along one hinged side. In other embodiments, access portals may be provided on a side surface of the container. The container may also comprise a secondary access portal, such as a mail slot 18, which permits a carrier to insert smaller items into the container 2 without a code. In this manner, routine deliveries (including, for example, daily mail) may be delivered and stored in the container without first requiring an access code to open the container. In one embodiment, the entry of a passcode may alert a user via a mobile application, including instances where the correct code or an incorrect code is supplied.

In one embodiment, the container comprises a first portion that is refrigerated (or temperature controlled) and is used for deliveries of perishable items, such as groceries, some pharmaceuticals, etc. The container may also comprise a freezer compartment or the temperature of the refrigeration compartment may be reduced for frozen items. Climate control/temperature of the device may be controlled by the user remotely, through wireless or other signal indications communicated to the container via the application described in detail below. The container preferably plugs into an electrical outlet located proximate to the container, such as an exterior household outlet. In certain embodiments, the container may further comprise a photovoltaic panel 22 for providing primary or auxiliary power to the container. The photovoltaic panel 22 may comprise an array of cells and be positioned in a manner to maximize the generation of solar power to the system, including by providing the array on a hinged surface proximate to the top surface of the container. Alternatively, the array may be located remotely from the container to account for the position of the sun relative to the porch, stoop, or entryway. The container may employ a backup battery-powered source. In certain embodiments, the user is notified when power is disconnected or if the backup battery becomes necessary to power the container.

Referring now to FIG. 2, the container may be positioned in a visible location on the front of a user's residence to best notify carriers of the container's presence and location, thereby increasing the accuracy of deliveries. The container may include the address numbers 26 and/or street name of the property to facilitate deliveries. The container may be movable from the location depicted, and a user may position the container in several different orientations best suited for the constraints of the property. In certain embodiments, the container includes other indicia and may comprise lighting to make it easier for a carrier to locate the container at a specific property. In certain embodiments, illumination may be provided to alert a carrier that a delivery is expected at the property, while a different illumination alert's the recipient that an item has been received in the container. The container may be larger or smaller in footprint than the container shown, and in some embodiments may have a greater height than depicted.

RFID or other tracking circuits or coils may be provided for identifying the package and items therein. Packages and/or containers may comprise GPS location tracking tags, which allow a user or carrier to pinpoint the desired location of the package or container relative to the address and route the package or container through the optimal delivery network. Additionally, the containers described above may have the ability to sense the size of the package or portable container arriving for a specific delivery and further sense the temperature and/or humidity requirements for perishable items. The combination of security and loss-mitigation features of the systems described herein allow a carrier or user to virtually eliminate risk of spoilage and theft.

A solar array may also be provided for providing power to the unit for preventing spoilage, for example, through a refrigeration unit associated with the container. The containers may have unique codes (through RFID circuits or otherwise) and may be configured to be received within a certain container at a user's residence. In embodiments, the portable container may comprise other indicia to help with identifying the package or the items associated therewith. Multiple carriers may be provided with access to the container of the embodiments described herein.

In embodiments, the system facilitates communications with one or more IoT devices. This communication may occur over a local system. Preferably, each IoT device in a local system is configured for remote control and communication with a user. IoT devices may include cameras or other security equipment, scales, sensors, locks (including door locks and electronic locks), garage door openers, doorbell monitors, and other devices. In alternate embodiments, the communication occurs over a wide area network. In embodiments, the network may be a private network, while in other embodiments the network may be a public network. The devices configured over the network are preferably capable of receiving inputs and communicating changes in state to at least a user associated with the property where a container is located, although it may also be configured to communicate to a carrier. Variations on the network and device configurations are contemplated herein. For example, a carrier may be allowed access to control a garage door opener to permit partial or complete access to a space located within a user's garage for placing an item therein. In other applications, a carrier may be allowed to enter a unique code to access a container. Autonomous delivery vehicles may also include these allowances.

FIGS. 3 and 4 show sectional views of the container 2. As in the embodiments described above, the container 2 includes an access portal 14 that allow selective entry into the container's internal volume. In addition, the refrigeration unit 30 is shown in FIG. 3. The container 2 may also include handles 34 that facilitate container movement. Container 2 may further comprise a motor 28, such as a servo or stepper motor, to actuate one or more doors to the interior of the container 2. In alternative embodiments, the motor 28 may be a pneumatically operable device and actuated by Referring to FIG. 5, embodiments of the present disclosure provide a user with the option to provide a door 35 as an access portal for transferring items to the user. For example, a keypad 32 located on or near a door 35 to a user's garage 36 may provide a carrier with access to a partitioned section of the user's garage 36 for storing deliveries. The garage partition and accessible from the exterior of the garage may be large enough to provide a freezer, refrigerator or like equipment for receiving perishable items. The door 35 may provide access to a sufficient space for delivering large items such as sporting equipment, furniture, exercise equipment or similarly-sized items. The embodiment of FIG. 5 may comprise similar functionality as the embodiments of FIGS. 1-4.

Figure 5:
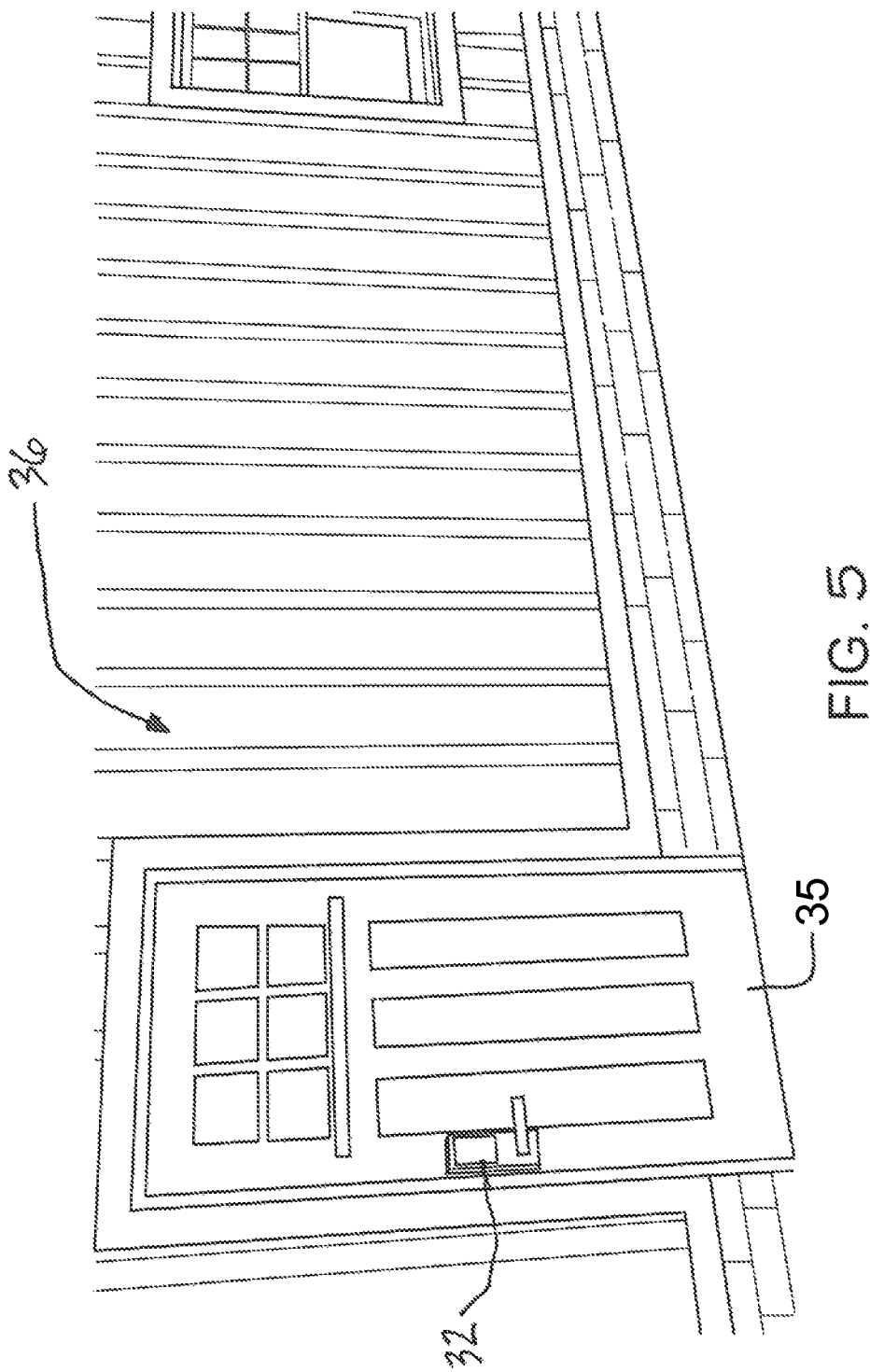
FIGS. 5-6 illustrate embodiments of the present disclosure wherein the secure location may be within a secure portion of a residential property such as a garage.

Additional security may be provided with the embodiment of FIG. 5. For example, a video surveillance system may be provided with the keypad access control to ensure that the items stored in the partitioned section of the user's garage 36 are not disturbed, and to further ensure that no one without access to the remainder of the property inadvertently or intentionally gains access to the remainder of the property. Additional security that may be provided in this and other embodiments includes RFID readers/scanners, chip readers, infrared scanners, proximity scanners, biometric scanner or other security apparatus known to those of ordinary skill in the art.

Figure 6:
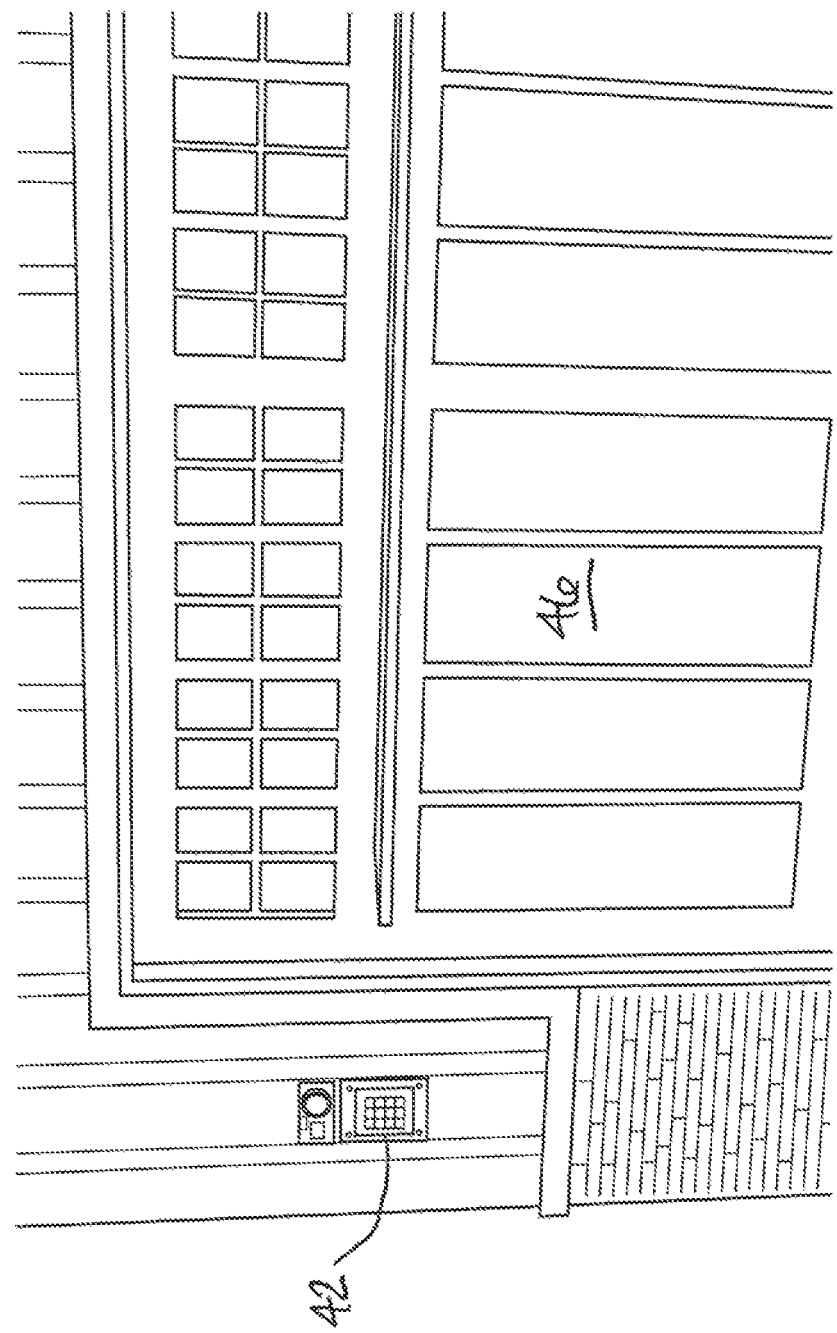

Referring now to FIG. 6, a keypad 42 may alternatively be located near the garage door 46 and permit an authorized passcode holder to raise the garage door 46 for temporary access to the garage. In this embodiment, a portion of the garage may still be partitioned to avoid access to other items already stored in the garage. The main garage may also comprise a refrigerator or freezer for storing perishable items. The garage door 46 may also be provided with a timing circuit or proximity sensors so that the garage door 46 is automatically closed after the passage of time and/or the presence of movement in the garage is no longer detected.

Figure 7:
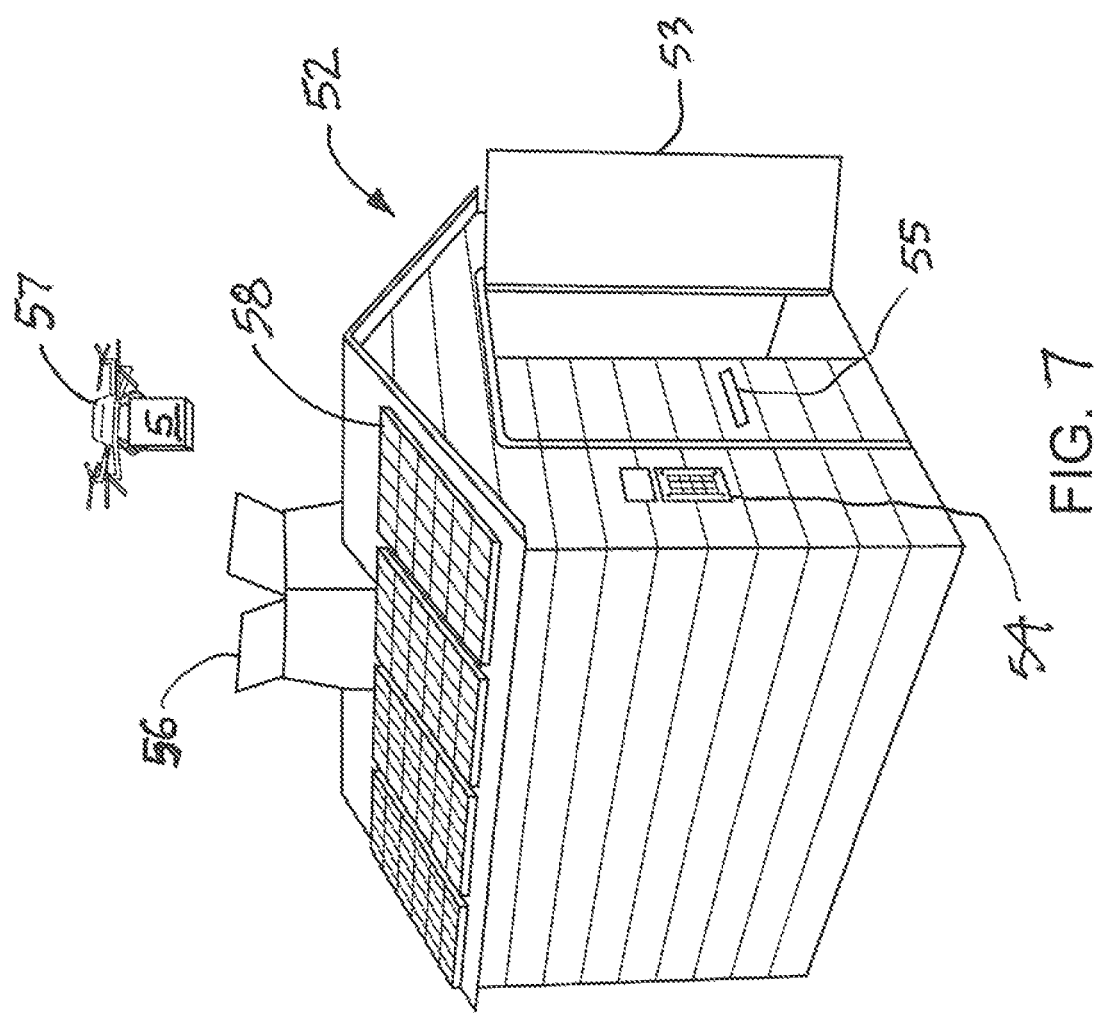
FIG. 7 illustrates embodiments of the present disclosure wherein the secure location is a remote structure, such as a shed.

Turning now to FIG. 7, in certain embodiments, the container may be comprised of a shed 52 or similar structure on the user's property. In this embodiment, the access portal 56 may be located on the roof of the structure and permit an autonomous delivery vehicle (i.e., a drone) 57 to deliver an item 5 to the container/shed 52 from the air. This access permits a user to provide a large storage space for receiving deliveries while maintaining strong security over the access portal 56. The access portal 56 may comprise retractable panels or doors that open only when an authorized delivery is in the proximity of the container/shed 52. In certain embodiments, the access portal 56 further comprises an elevated platform that can receive parcels in a first position and then retract towards the floor of the container/shed 52 once the parcel is placed on the platform. The structure may further comprise electrical outlets as described above for powering refrigeration or freezing equipment and may also comprise a photovoltaic system 58 for providing power to the container/shed 52 or equipment located therein. The container/shed 52 may also provide access through a door or doors 53, which may be securely controlled through the use of a keypad 54 or other security measures described herein. The container/shed 52 may also comprise a second access portal 55 for receiving regular items, such as mail.

Figure 8:
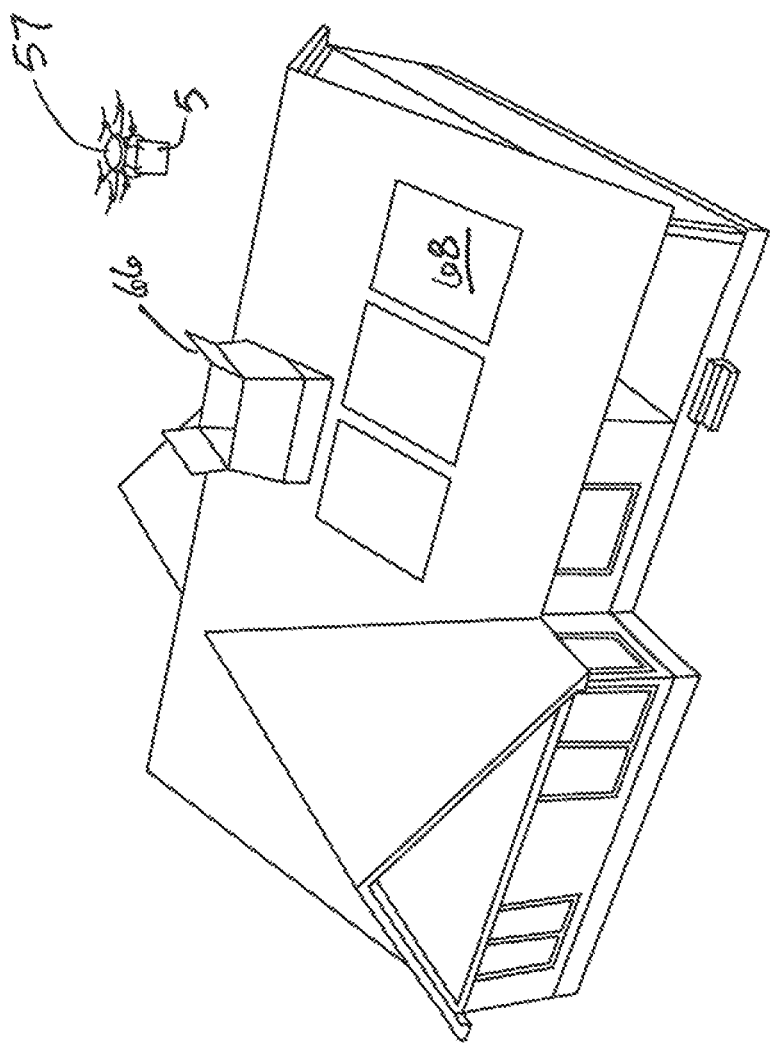
FIG. 8 illustrates embodiments of the present disclosure wherein the secure location is accessible from a roof or attic.

The embodiment shown in FIG. 8 is similar to the embodiment of FIG. 7, with a roof-mounted container 66 located on the roof surface of a structure. Here, the structure is a single-family residence. However, in other embodiments, the roof-mounted container may be provided on an apartment building or condominium or other structure. The container 66 preferably provides access to an attic or other area where items may be stored and may have retractable doors as described above, or may be lowered to a main floor via an elevator-like or dumbwaiter-like system. This embodiment provides heightened security as access to the roof-mounted container 66 is limited to autonomous delivery vehicles 57. Solar or photovoltaic systems 68 may also be provided for supplying or augmenting power requirements of the system.

Figure 9:
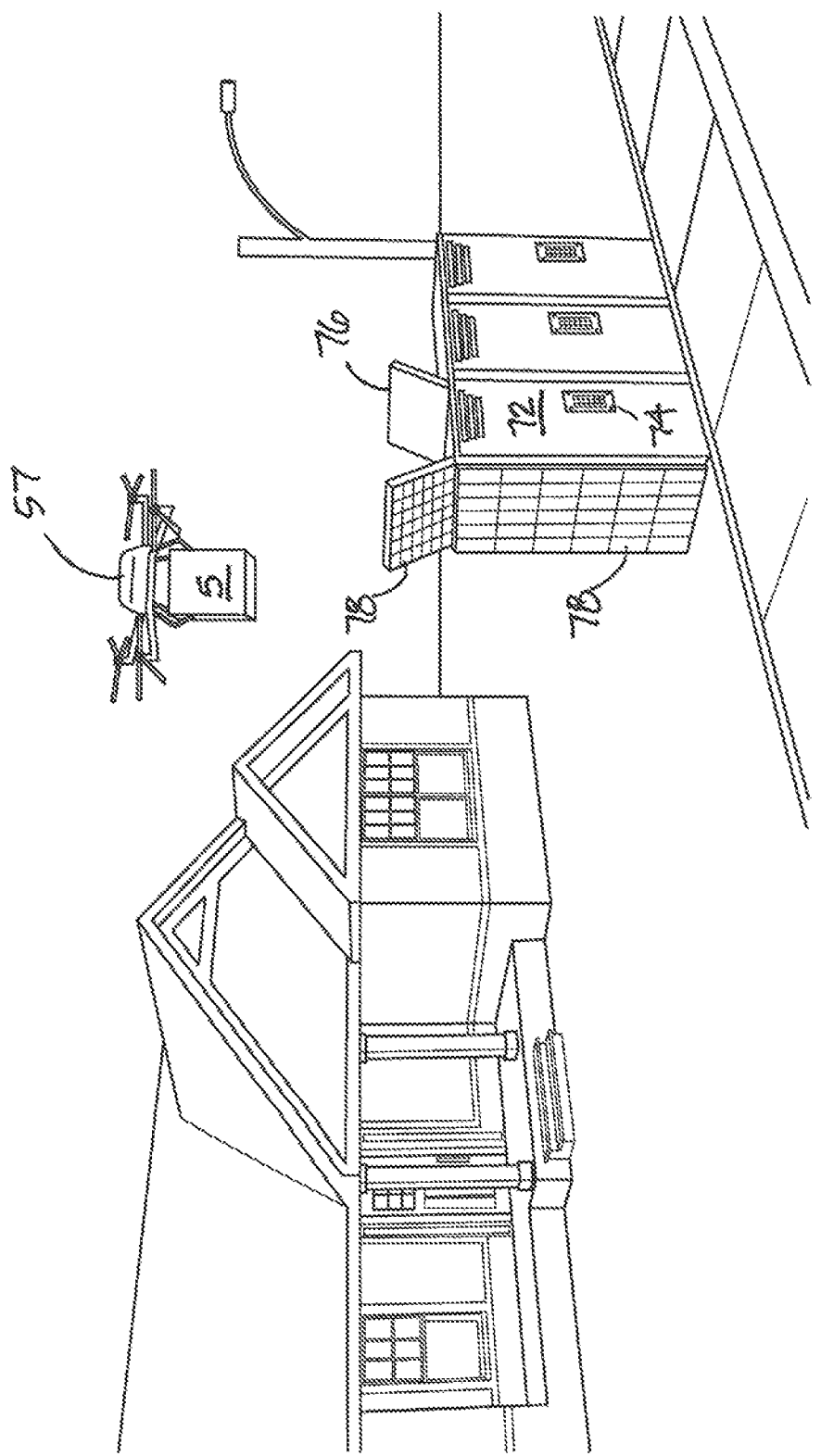
FIG. 9 illustrates embodiments of the present disclosure wherein the secure location is located on a street, sidewalk, driveway or curb.

In FIG. 9, the container 72 may be located on a curb or similar location and may comprise a user-owned container 72 among several containers, for example. In other embodiments, the container 72 may be owned by a municipality or a carrier, and temporarily assigned to a recipient of an item who lives proximate to the container 72. The containers 72 may comprise a top-sided access portal 76 for receiving items 5 therein, although other locations of the access portal 76 are contemplated, and may also comprise a photovoltaic system 78 for providing power. Although the containers 72 may be at ground level, in certain embodiments the container 72 may be recessed in a portion of a sidewalk or driveway, for example, thereby permitting the container 72 to be visible only when an authorized item 5 arrives for delivery. In this embodiment, the container 72 may be positioned on an elevated platform and extendable through access doors, which can open and close automatically when an item 5 arrives for delivery as shown in FIG. 9. The doors are preferably configured to close automatically once the platform is lowered and the item(s) 5 secured in the container 72.

Figure 10:
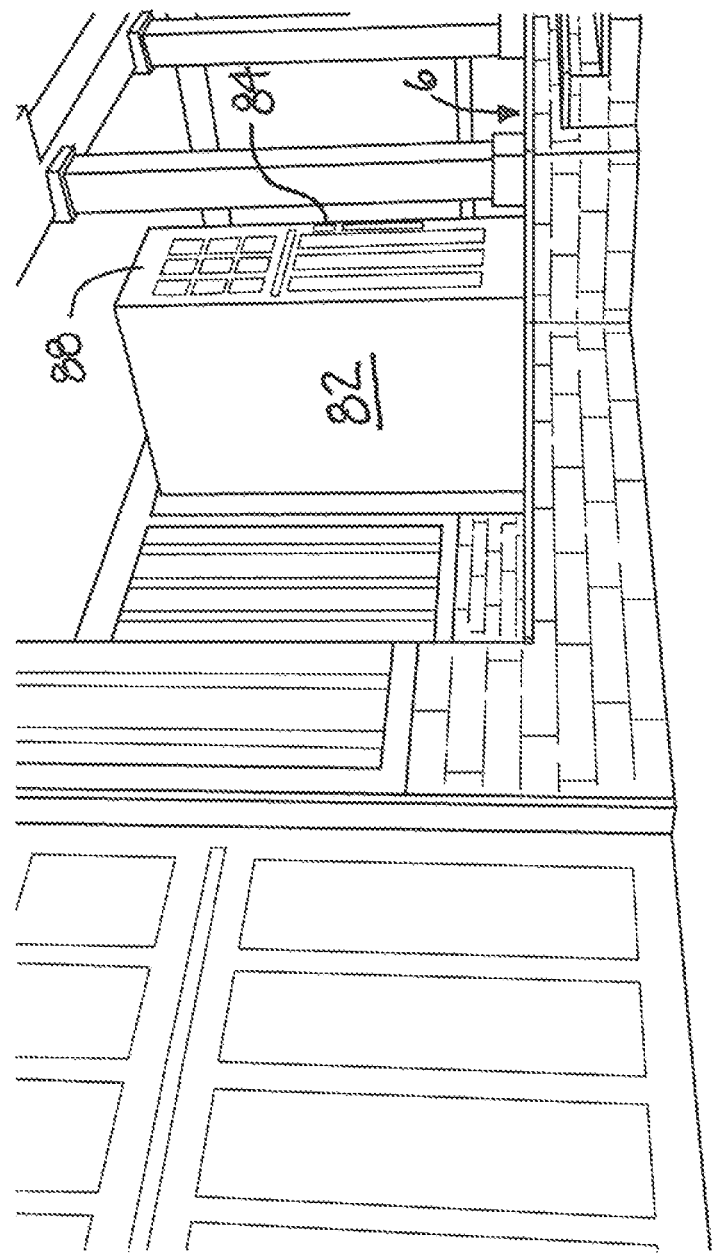
FIGS. 10-11 illustrate embodiments of the present disclosure wherein the secure location is a vestibule, doorway, or equivalent location.
Figure 11:
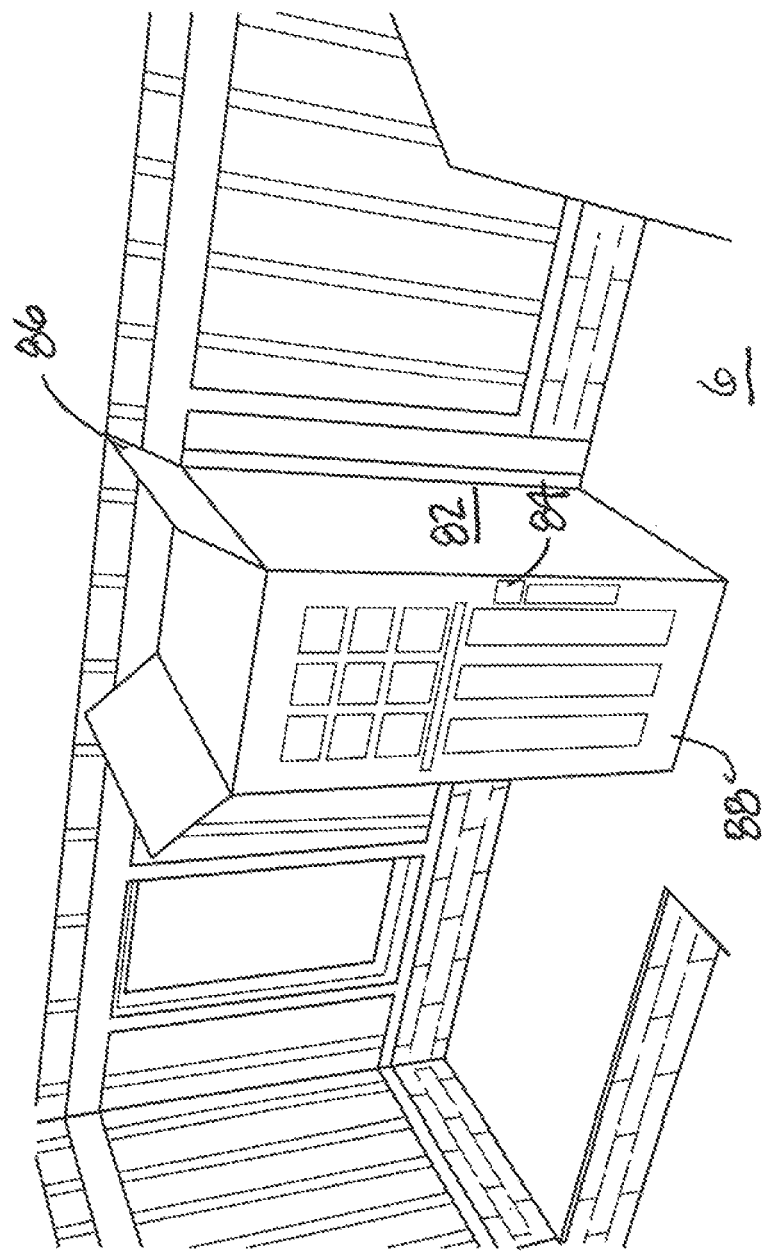

The embodiment of FIGS. 10-11 is similar to the embodiments of FIGS. 1-2. In FIG. 10, the container is shown as a vestibule 82 with a full-height (or equivalent) door 88 that serves as the access portal. The door 88 may be accessible via a keypad 84 as described above or may have other security means. A smart lock may be provided with the doorknob as well. The vestibule 82 may be located on a porch 6 or other secure area of a user's property. A portion of the container may have a temperature-controlled container for perishable items. As shown in FIG. 11, the vestibule 82 may have a retractable roof opening 86 that serves as the access portal and may be operated in a manner similar to that described in relation to FIG. 7. This may be desirable for entryways that do not have an overhang or canopy above the entry.

Figure 12:
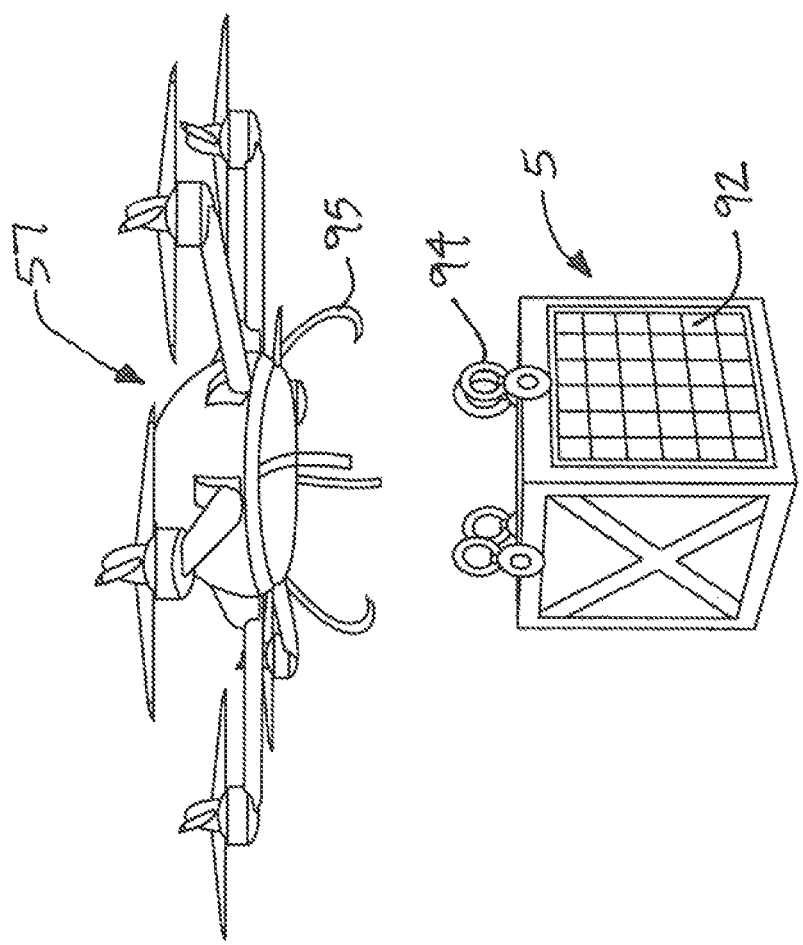
FIG. 12 illustrates embodiments of the present disclosure wherein a portable shipping container may be transported to any residential, commercial or industrial location.

The embodiment of FIG. 12 comprises a portable container 5 for shipping items, including via an autonomous delivery vehicle (i.e., drone) 57 and may be used in conjunction with any of the embodiments described above. The container 5 preferably comprises a plurality of hooks or latches 94 for securing to tethers or other apparatus 95 associated with a drone 57 and can be used to transport the container to a desired destination. The portable container 5 may come in a variety of sizes but preferably is large enough to transport standard size items for a particular carrier. The container 5 may comprise reinforcing members to ensure items located therein are not damaged if the container comes into contact with the storage containers described above. In certain embodiments, the container 5 may further comprise a photovoltaic system(s) for powering the container 5. The container 5 may be engineered to be weatherproof as well as extremely durable and reusable, thus potentially cutting down on cardboard and packaging waste. Container 5 may be used for delivery to high-rise apartments, condominiums, commercial properties and other properties that are not single-family residences. In this manner, the aspects of the system described herein may be realized for other types of property owners.

RFID or other tracking circuits or coils may be provided for identifying the parcel and items therein. Parcels and/or containers may comprise GPS location tracking tags, which allow a user or carrier to pinpoint a desired location of the parcel or container relative to the address and route the parcel or container through the optimal delivery network. Additionally, the containers described above may have the ability to sense the size of the parcel or portable container arriving for a specific delivery and further sense the temperature and/or humidity requirements for perishable items. The combination of security and loss-mitigation features of the systems described herein allow a carrier or user to greatly reduce if not eliminate the risk of spoilage and theft.

A solar array may also be provided for providing power to the unit for preventing spoilage, for example, through a refrigeration unit associated with the container. The containers may have unique codes (through RFID circuits or otherwise) and may be configured to be received within a certain container at a user's residence. In embodiments, the portable container 5 may comprise other indicia to help with identifying the parcel or the items associated therewith. Containers like the one shown in FIG. 12 may be provided to multiple different carriers and used in conjunction with any of the embodiments described herein.

FIG. 13 illustrates an embodiment of the present disclosure for transporting business or consumer items in a commercial container 102, which may comprise different and various sizes. The commercial container 102 may comprise a keypad 104 for accessing through a set of doors 103 or may further comprise an opening 106 similar to the embodiment of FIG. 7 for delivery directly to the commercial container 102 by a drone, robot, etc. (not shown in FIG. 13) or equivalent autonomous delivery device. The commercial container 102 may have any of the aforementioned features and benefits of the embodiments described above.

The description above sets forth various levels of detail regarding the varying embodiments. It is to be expressly understood that no limitation as to the scope of this disclosure is intended by either the inclusion or non-inclusion of elements, components, etc. in the Detailed Description. In certain embodiments, components or sub-components have been grouped and discussed in connection with certain embodiments while not being described in others. This is for the purpose of streamlining the disclosure and is not intended to disavow or surrender any scope of the present disclosure.

In some embodiments, the systems and methods described above may be provided via an application comprising one or several modules. In one embodiment, the application/modules are designed to operate on a mobile device or mobile computer and assist a user with managing delivery, transfer, receipt, and acceptance of items to one or more containers. In embodiments, the application is advantageously configured to receive and send information by, for example, a recipient's mobile device. In one embodiment, the application comprises one or more user interfaces and displays. For example, the system further comprises the ability to graphically display the status of events or actions associated with a container, including actions requested by a carrier, for example, and items received at a container so that the delivery, transfer, and retrieval of items can be efficiently managed.

According to some embodiments, the system is configured to permit secure messaging between users. For example, secure messaging between a first user and another individual may be provided for notifying a user of a request for access or to confirm a subsequent action has been taken, such as closing the access portal and securing the items in the container. This messaging may be manually initiated, but in a preferred embodiment occurs automatically when an item arrives at the location of a container associated with the user. The messaging may be provided through a mobile application residing on a recipient's mobile device, for example.

In one embodiment, the application/modules may comprise one or more data sets, tables or databases, including one or more relational databases. In one embodiment, the application includes time and/or delivery-specific alerts and/or notifications. In embodiments, the application/modules further permit a user to sort, search and modify delivery records or events and thereby add or revise data associated therewith.

The modules and applications described herein are preferably configured to run on a computer server or similar computational machinery. The application may be configured to provide notifications or alerts. Alerts may be provided via the module, including via notification upon login and/or push notification, or via email, messaging, or other suitable methods of communication to the recipient. Alerts may be defined for certain conditions and customized by the user. Alternately, alerts may be provided for certain events or actions, such as unauthorized actions, regardless of the user's configuration. In some examples, an alert may indicate a recommended course of action. For example, the alert may recommend that additional action be taken.

According to some embodiments, the mobile application may further be configured to provide a user with the ability to filter and sort collective or individual item data. For example, the user may purchase groceries that have individually identifiable codes or indicia that the container may recognize. In embodiments, the recognition of items may occur through the incorporation of one or more RFID readers/scanners, chip readers, infrared scanners or proximity scanners, for example. In other embodiments, the container may be equipped with a scale or equivalent sensor to provide the user with the weight or size of the item(s) received in the container. The data obtained by the system may enable delivery services picking up a package from secure storage, which has been weighed and sized, for outbound delivery.

It is another aspect of some embodiments of the present disclosure to provide software, which in certain embodiments is in the form of a mobile application, provided with a computer-readable storage medium (preferably non-transitory) comprising processor-executable instructions operable to utilize the systems or perform the methods as described herein. The software may be installed on a mobile device that allows users to monitor and/or control container access. In some embodiments, a carrier may have certain use rights granted by the user and managed through the mobile application or a desktop-based application.

In some embodiments, the software solution includes, but is not restricted to, a mobile application, wherein a browser-based application that connects all the components of the complete product delivery value chain. The system may comprise an e-commerce website, the corresponding delivery service for the ordered product, and the relevant container or receptacle that accepts the delivery. All the components will preferably be connected to each other via a cloud computing platform, via Blockchain, local IoT networks, or via a mobile application configured to track and monitor status of system components as described herein. In other embodiments, the application will offer a one-click solution for providing the relevant delivery information like an order confirmation, tracking details, and communicate with the container, access authorization information from and to authorized delivery services or autonomous apparatus.

In some embodiments, the system may be used to transfer ownership of items between two private parties at a secure location or facilitate charitable donations. The system may permit the storing party to collect a small fee for the storage and use of a container that is controlled by the storing party or another third party, such that the owner of the container can generate revenue from the use of the container by others.

Embodiments of the present invention improve on this method by also including an indication of the container's location. When the human or automated carrier scans the package and forwards that information to the container, or when the container scans or otherwise recognizes the package, the container opens to receive the package. Thereafter, the system notifies the recipient that the package has been delivered and secures the container. Accordingly, continuous and secure package delivery is possible.

It is one aspect of some embodiments to provide a delivery and receipt system, which protects one or more packages from external elements, allows for secure handoff/notification, secure storage, and, in some embodiments, climate control to keep refrigerated or frozen items cold and fresh. The refrigerated storage compartment employed by some embodiments receives power via a direct connection to the dwelling's power or a battery. In other embodiments, dedicated solar panels are provided. In some embodiments, the system will employee scales, cameras, or other sensors to recognize weight, volume, and temperature of the contents inside to trigger a refrigeration or freezer element if needed. Alternative delivery methods are also contemplated that enable seamless driverless vehicle, robot, and/or drone delivery. Additionally, standard mail can be delivered in a dedicated slot, while in still other embodiments the box may come attached with a folded wire mesh that can be opened up to drop off large packages which do not fit inside and secured using a self-locking device.

Accordingly, the systems and methods of the present disclosure provide for secure delivery, transfer of ownership, storing, accessing and receiving an item from another. In one embodiment, a system and method are provided to securely receive a variety of different sizes and types of parcels at one or more locations, including but not limited to on or adjacent a recipient's property. In yet other embodiments, the system and method permits a user to track the shipment and delivery of a parcel and confirm receipt of the same from any location, thereby ensuring that the parcel has arrived at the correct location and is securely stored until the user returns to the delivery location to retrieve the item. In further embodiments, the system may comprise an interactive modality for receiving and granting access to a container that is owned or at least temporarily dedicated to a particular user. And in other embodiments, the system and method allow a user to receive and store an item without exposing the item to loss, damage, spoilage or other events that would impair the value of the items.

Additionally, the components of the system are designed such that if the need arises to have a larger box, then an additional modular attachment can vertically increase the size of the box with simple assembly. In this embodiment, the lid of the box detaches and the modular attachment fits onto the top of the box making the box taller while the breadth and the width remain the same. The lid then fits onto to the top of the modular attachment to make the box complete and fully functional. In another embodiment, the same is done through horizontal modular expansion from the side, increasing the width. This modular expansion may apply in both residential and commercial application.

In embodiments, a delivery ecosystem is provided that makes it easier to schedule and receive and store deliveries to any residential, commercial or industrial property, including by way of the communication of information (preferably via the mobile application) from the delivery service provider or autonomous delivery apparatus to the party receiving the items. The recipient can access the system via the application and monitor and approve delivery of items, including those that require refrigeration or signature from the recipient prior to deposit in a secure container or secure location. New customers can register with the mobile application and route all deliveries through the application, which in turn provides detailed information to the delivery service regarding the secure location to deposit the items for delivery, track and confirm deposit of the items once the delivery service arrives at the property, and confirm secure receipt by the owner, thereby greatly mitigating if not preventing risk of loss or spoilage of the items while adding great convenience to the recipient. The mobile application allows the recipient to monitor the delivery and storage of the items and, if preferred, permit access to retrieve the items by an authorized party. In this manner, the recipient may use the system for returns or exchanges as well as receipt of originally purchased items. In embodiments, the system may be used for private party-to-party transactions and exchanges, including through accessible containers or other secure locations that may be leased by another but not necessarily at either party's residence. In this embodiment, items may be temporarily secured at a secure location for transfer at a safe and convenient time.

Methods for securely ordering or returning a package, tracking shipment and receipt or pick up and storage of an item, and eventual registration of receipt or pick up of an item are also disclosed. In one embodiment, the user initiates the method with the step of placing an order or pick up with specified instructions (location, access details). These instructions preferably include details beyond the ship-to or pick up address and may contain GPS location of the container to receive or pick up the delivery, an authorization code for opening the container, etc. Next, a carrier delivers or picks up the package to or at the location and identifies the container to receive or pick up the package. Upon a scan of the package and/or entry of the unique user-provided code, the container opens the access portal for receipt or pick up of the package and secures the access portal after the package is confirmed to be placed within the container or picked up for returns. Then the container may be configured to communicate its secure state to the recipient and the carrier immediately after delivery.

The system includes the step of scheduling deliveries, pick up or returns at any time of day (as acceptable to the customer or delivery company). The customer does not have to be present in a constrained time period to receive or handover or condition (move to refrigerator/freezer) received goods. The step of scheduling delivery for a certain time is also as option.

The methods described above may continuously flow in a loop, flow according to a timed event or sequence, or flow according to a change in status. The method may be initiated or suspended by a user at various times during the method described above. In certain embodiments, the methods may be performed automatically or semi-automatically.

The application, modules and associated user interfaces described herein may be stored or operated on a computing environment, wherein the systems, devices, servers, modules, etc. may execute. The computing environment preferably includes one or more user computers. The computers may be general-purpose personal computers (including, merely by way of example, personal computers, and/or laptop computers running various versions of Microsoft Corp.'s Windows™ or other operating systems) and/or workstation computers running any of a variety of commercially-available UNIX™ or UNIX-like operating systems. These user computers may also have any of a variety of applications, including, for example, database client and/or server applications, and web browser applications. Alternatively, the user computers may be any other electronic device, such as a thin-client computer, Internet-enabled mobile telephone, and/or personal digital assistant, capable of communicating via a network and/or displaying and navigating web pages or other types of electronic documents. Any number of user computers may be supported.

The computing environment described according to this embodiment preferably includes at least one network. The network can be any type of network familiar to those skilled in the art that can support data communications using any of a variety of commercially-available protocols, including without limitation SIP, TCP/IP, SNA, IPX, AppleTalk, and the like. Merely by way of example, the network may be a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth™ protocol known in the art, and/or any other wireless protocol); and/or any combination of these and/or other networks.

The system in varying embodiments may also include one or more server computers. One server may be a web server, which may be used to process requests for web pages or other electronic documents from user computers. The web server can be running an operating system including any of those discussed above, as well as any commercially-available server operating systems. The web server can also run a variety of server applications, including SIP servers, HTTP servers, FTP servers, CGI servers, database servers, Java servers, and the like. In some instances, the web server may publish operations available operations as one or more web services.

According to certain embodiments, the computing environment may also include one or more file and or/application servers, which can, in addition to an operating system, include one or more applications accessible by a client running on one or more of the user computers. The server(s) may be one or more general-purpose computers capable of executing programs or scripts in response to the user computers. As one example, the server may execute one or more web applications. The web application may be implemented as one or more scripts or programs written in any programming language, such as Java™, C, C#™, or C++, and/or any scripting language, such as Perl, Python, or TCL, as well as combinations of any programming/scripting languages. The application server(s) may also include database servers, including without limitation those commercially available from Oracle, Microsoft, Sybase™, IBM™ and the like, which can process requests from database clients running on a user computer.

In embodiments, the web pages or equivalent graphical displays created by the application server may be forwarded to a user computer or user mobile device via a web server. Similarly, the web server may be able to receive web page requests, web services invocations, and/or input data from a user computer and can forward the web page requests and/or input data to the web application server. In further embodiments, the server may function as a file server. Although the foregoing generally describes a separate web server and file/application server, those skilled in the art will recognize that the functions described with respect to servers may be performed by a single server and/or a plurality of specialized servers, depending on implementation-specific needs and parameters. The computer systems, file server and/or application server may function as an active host and/or a standby host.

In embodiments, the computing environment may also include a database that may or may not use Blockchain. The database may reside in a variety of locations. By way of example, database may reside on a storage medium local to (and/or resident in) one or more of the computers. Alternatively, it may be remote from any or all of the computers, and in communication (e.g., via the network) with one or more of these. In a particular embodiment, the database may reside in a storage-area network ("SAN") familiar to those skilled in the art. Similarly, any necessary files for performing the functions attributed to the computers may be stored locally on the respective computer and/or remotely, as appropriate. In one set of embodiments, the database may be a relational database, which is adapted to store, update, and retrieve data in response to SQL-formatted commands.

The computer system may also comprise software elements, including but not limited to application code, within working memory, including an operating system and/or other code. It should be appreciated that alternate embodiments of a computer system may have numerous variations from that described above. For example, customized hardware might also be used and/or particular elements might be implemented in hardware, software (including portable software, such as applets), or both. Further, connection to other computing devices such as network input/output devices may be employed.

In embodiments, one or more web servers are operable to provide web services to the user devices. In embodiments, the web server receives data or requests for data and communicates with the database server to store or retrieve the data. As such, the web server functions as the intermediary to put the data in the database into a usable form for the user devices. There may be more or fewer web servers, as desired by the operator.

In this embodiment, a database server is any hardware and/or software operable to communicate with the database and to manage the data within the database. Database servers, for example, SQL server, are well known in the art. The database can be any storage mechanism, whether hardware and/or software, for storing and retrieving data.

In the foregoing description, for the purposes of illustration, systems and methods were described in a particular order. It should be appreciated that in alternate embodiments, the methods may be performed in a different order than that described. It should also be appreciated that the methods described above may be performed by hardware components or may be embodied in sequences of executable instructions on machine-readable media, and which cause a machine, such as a general-purpose or special-purpose processor or logic circuits programmed with the instructions to perform the methods. These machine-executable instructions may be stored on one or more machine-readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments have been described as a process, which in materials supplied herewith is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed but could have additional steps not included in the figure. A process may correspond to a method, a function, a procedure, a subroutine, a subprogram, etc.

When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine-readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While various embodiments of the present invention have been described in detail, it is apparent that modifications and alterations of those embodiments will occur to those skilled in the art. It is to be expressly understood that such modifications and alterations are within the scope and spirit of the present invention, as set forth in the following claims. Further, it is to be understood that the invention(s) described herein is not limited in its application to the details of construction and the arrangement of components set forth in the preceding description or illustrated in the drawings. The invention is capable of other embodiments and of being practiced or of being carried out in various ways. Also, it is to be understood that the phraseology and terminology used herein is for the purpose of description and should not be regarded as limiting. Further, any one or more of the aspects/embodiments as substantially disclosed herein optionally in combination with any one or more other aspects/embodiments as disclosed herein.

What is claimed is:

1. A method of securely receiving and storing a package, comprising:
    providing a selectively openable container that includes a data input device;
    identifying or sensing the presence of the package or carrier when the package is a predetermined distance from the container, and at least one of:
        transmitting a notification to a recipient, and
        transmitting a notification to a carrier that the container is near;
    obtaining data with the data input device;
    verifying the data;
    conducting a package receipt sequence that comprises at least one of:
        verifying the package can fit within the container, and
        verifying the package is intended for receipt;
    unlocking the container if the data meets predefined criteria;
    accepting the package within the container;
    closing the container;
    locking the container;
    disinfecting an interior volume of the container automatically after locking the container or after locking the container only upon recipient direction; and
    wherein the container generates at least one notification to the recipient indicating at least one of the following:
        that the container has been accessed,
        that the package has been delivered,
        that the package has been disinfected, and
        that the container is closed and locked.

2. The method of claim 1, wherein disinfecting the interior volume of the container comprises exposing the package to a mist of disinfectant, a disinfecting environment, air that includes a disinfectant, ultra-violet radiation, a vacuum, an inert gas, an increase of temperature above a predetermined degree for a predetermined amount of time, or a decrease in temperature below a predetermined degree for a predetermined amount of time.

3. The method of claim 2, wherein the predetermined amount of time is defined by a carrier, the recipient, or a third party.

4. The method of claim 1, wherein disinfecting the interior volume of the container comprises at least two of exposing the package to a mist of disinfectant, a disinfecting environment, air that includes a disinfectant, ultra-violet radiation, a vacuum, an increase of temperature above a predetermined degree for a predetermined amount of time, or a decrease in temperature below a predetermined degree for a predetermined amount of time.

5. The method of claim 1, further comprising testing the package or air within the container to verify the absence of pathogen or to identify the number of pathogens present on the package.

6. The method of claim 5, wherein the container remains locked until the amount of pathogens present on the package or in the air within the container is below a predetermined level.

7. The method of claim 5, further comprising performing further disinfecting if the amount of pathogens on the package or in the air within the container is above a predetermined level.

8. The method of claim 7, wherein initial disinfecting comprises at least one of exposing the package to a mist of disinfectant, a disinfecting environment, air that includes a disinfectant, ultra-violet radiation, a vacuum, an increase of temperature above a predetermined degree for a predetermined amount of time, and a decrease in temperature below a predetermined degree for a predetermined amount of time;
    wherein further disinfecting comprises at least one of exposing the package to a mist of disinfectant, a disinfecting environment, air that includes a disinfectant, ultra-violet radiation, a vacuum, an increase of temperature above a predetermined degree for a predetermined amount of time, and a decrease in temperature below a predetermined degree for a predetermined amount of time; and
    wherein the method of initial disinfecting and further disinfecting are different.

9. The method of claim 1, wherein the container includes at least one monitoring device, and further comprising obtaining at least one of package temperature, package weight, package integrity, and package shape with the at least one monitoring device.

10. A method of securely receiving and storing a package, comprising:
    providing a selectively openable container that includes a data input device;
    obtaining data with the data input device;
    verifying the data;
    unlocking the container if the data meets predefined criteria;
    accepting the package within the container;
    closing the container;
    locking the container;

disinfecting an interior volume of the container, wherein the container remains locked until the amount of pathogens present on the package or in the air within the container is below a predetermined level; and wherein the container generates at least one notification to the intended recipient indicating at least one of the following:
that the container has been accessed,
that the package has been delivered,
that the package has been disinfected, and
that the container is closed and locked.

11. The method of claim 10, wherein disinfecting the interior volume of the container comprises exposing the package to a mist of disinfectant, a disinfecting environment, air that includes a disinfectant, ultra-violet radiation, a vacuum, an inert gas, an increase of temperature above a predetermined degree for a predetermined amount of time, or a decrease in temperature below a predetermined degree for a predetermined amount of time.

12. The method of claim 10, further comprising testing the package or air within the container to verify the absence of pathogen or to identify the number of pathogens present on the package.

13. A container configured to selectively receive at least one package, comprising:
a storage space;
a selectively openable door associated with the storage space having a closed positon of use and an open position of use;
a lock associated with the door, the lock maintaining the door in the closed position of use;
at least one nozzle that selectively releases a disinfecting mist, at least one ultra-violet radiation emitter, a heater, and a refrigeration unit;
a data input device in communication with the lock, wherein the lock will release and allow the door to transition to the open position of use when the data input device receives predetermined data;
a power source interconnected to the data input device;
a communications device configured to communicate at least one of:
that the container has been accessed,
that the package has been delivered,
that the container is closed and locked, and
that the package has been disinfected; and
a controller that communicates with the at least one nozzle that selectively releases a disinfecting mist, at least one ultra-violet radiation emitter, a heater, and a refrigeration unit, wherein the controller configured to at least one of initiate locking of the container, initiate package disinfection, control disinfecting time, and communicate with a sensor configured to test the package or air within the container to verify the absence of pathogen or to identify the amount of pathogens present on the package.

14. The container of claim 13, further comprising at least one of an alarm and a light.

15. The container of claim 13, further comprising at least one monitoring device configured to obtain at least one of package temperature, package weight, package integrity, and package shape.

16. A method of securely receiving and storing a package, comprising:
providing a selectively openable container that includes a data input device;
identifying or sensing the presence of the package or carrier when the package is a predetermined distance from the container, and at least one of:
transmitting a notification to a recipient, and
transmitting a notification to a carrier that the container is near;
obtaining data with the data input device;
verifying the data;
conducting a package receipt sequence that comprises at least one of:
verifying the package can fit within the container, and
verifying the package is intended for receipt;
unlocking the container if the data meets predefined criteria;
accepting the package within the container;
closing the container;
locking the container;
disinfecting an interior volume of the container;
wherein the container generates at least one notification to the recipient indicating at least one of the following:
that the container has been accessed,
that the package has been delivered,
that the package has been disinfected, and
that the container is closed and locked; and
wherein disinfecting the interior volume of the container comprises exposing the package to a mist of disinfectant, a disinfecting environment, air that includes a disinfectant, ultra-violet radiation, a vacuum, an inert gas, an increase of temperature above a predetermined degree for a predetermined amount of time, or a decrease in temperature below a predetermined degree for a predetermined amount of time defined by a carrier, the recipient, or a third party.

17. The method of claim 16, further comprising testing the package or air within the container to verify the absence of pathogen or to identify the number of pathogens present on the package.

18. The method of claim 17, wherein the container remains locked until the amount of pathogens present on the package or in the air within the container is below a predetermined level.

19. A method of securely receiving and storing a package, comprising:
providing a selectively openable container that includes a data input device;
identifying or sensing the presence of the package or carrier when the package is a predetermined distance from the container, and at least one of:
transmitting a notification to a recipient, and
transmitting a notification to a carrier that the container is near;
obtaining data with the data input device;
verifying the data;
conducting a package receipt sequence that comprises at least one of:
verifying the package can fit within the container, and
verifying the package is intended for receipt;
unlocking the container if the data meets predefined criteria;
accepting the package within the container;
closing the container;
locking the container;
disinfecting an interior volume of the container;
wherein the container generates at least one notification to the recipient indicating at least one of the following:
that the container has been accessed,
that the package has been delivered, that the package has been disinfected, and
that the container is closed and locked;
further comprising testing the package or air within the container to verify the absence of pathogen or to identify the number of pathogens present on the package; and
wherein the container remains locked until the amount of pathogens present on the package or in the air within the container is below a predetermined level.

20. The method of claim 19, wherein disinfecting the interior volume of the container comprises exposing the package to a mist of disinfectant, a disinfecting environment, air that includes a disinfectant, ultra-violet radiation, a vacuum, an inert gas, an increase of temperature above a predetermined degree for a predetermined amount of time, or a decrease in temperature below a predetermined degree for a predetermined amount of time.

21. The method of claim 19, further comprising testing the package or air within the container to verify the absence of pathogen or to identify the number of pathogens present on the package.

22. The method of claim 21, wherein the container remains locked until the amount of pathogens present on the package or in the air within the container is below a predetermined level.

23. The method of claim 21, further comprising performing further disinfecting if the amount of pathogens on the package or in the air within the container is above a predetermined level.

24. A method of securely receiving and storing a package, comprising:
providing a selectively openable container that includes a data input device;
identifying or sensing the presence of the package or carrier when the package is a predetermined distance from the container, and at least one of:
transmitting a notification to a recipient, and
transmitting a notification to a carrier that the container is near;
obtaining data with the data input device;
verifying the data;
conducting a package receipt sequence that comprises at least one of:
verifying the package can fit within the container, and
verifying the package is intended for receipt;
unlocking the container if the data meets predefined criteria;
accepting the package within the container;
closing the container;
locking the container;
disinfecting an interior volume of the container;
wherein the container generates at least one notification to the recipient indicating at least one of the following:
that the container has been accessed,
that the package has been delivered,
that the package has been disinfected, and
that the container is closed and locked;
further comprising performing further disinfecting if the amount of pathogens on the package or in the air within the container is above a predetermined level;
wherein initial disinfecting comprises at least one of exposing the package to a mist of disinfectant, a disinfecting environment, air that includes a disinfectant, ultra-violet radiation, a vacuum, an increase of temperature above a predetermined degree, and a decrease in temperature below a predetermined degree for a predetermined amount of time;
wherein further disinfecting comprises at least one of exposing the package to a mist of disinfectant, a disinfecting environment, air that includes a disinfectant, ultra-violet radiation, a vacuum, an increase of temperature above a predetermined degree, and a decrease in temperature below a predetermined degree for a predetermined amount of time; and
wherein the method of initial disinfecting and further disinfecting are different.

* * * * *